United States Patent
Smith et al.

(10) Patent No.: US 9,844,670 B2
(45) Date of Patent: Dec. 19, 2017

(54) COMPLEX STIMULATION CHANNEL ARRANGEMENTS

(71) Applicant: Cochlear Limited, Macquarie University, NSW (AU)

(72) Inventors: Zachary Mark Smith, Greenwood Village, CO (US); Christopher Joseph Long, Centennial, CO (US); Jan Raymond Janssen, St. Ives (AU)

(73) Assignee: Cochlear Limited, Macquarie University, NSW (AU)

( * ) Notice: Subject to any disclaimer, the term of this patent is extended or adjusted under 35 U.S.C. 154(b) by 36 days.

(21) Appl. No.: 14/971,059

(22) Filed: Dec. 16, 2015

(65) Prior Publication Data

US 2016/0175592 A1 Jun. 23, 2016

Related U.S. Application Data

(60) Provisional application No. 62/096,193, filed on Dec. 23, 2014.

(51) Int. Cl.
*A61N 1/36* (2006.01)
*A61N 1/05* (2006.01)

(52) U.S. Cl.
CPC ..... *A61N 1/36032* (2013.01); *A61N 1/36036* (2017.08); *A61N 1/0541* (2013.01); *A61N 1/36185* (2013.01)

(58) Field of Classification Search
CPC .. A61N 1/36; A61N 1/36032; A61N 1/36185; A61N 1/0541

(Continued)

(56) References Cited

U.S. PATENT DOCUMENTS 7,317,944 B1 1/2008 Overstreet
7,860,573 B2 12/2010 van den Honert
(Continued)

OTHER PUBLICATIONS

Zwolan et al., "Electrode discrimination and speech recognition in postlingually deafened adult cochlear implant subjects", Acoustical Society of America, J. Acoust. Soc. Am. 102 (6), Dec. 1997, 13 pages.

(Continued)

*Primary Examiner* — Carl H Layno
*Assistant Examiner* — Jon Eric C Morales
(74) *Attorney, Agent, or Firm* — Edell, Shapiro & Finnan, LLC

(57) ABSTRACT

Presented herein are techniques for determining an arrangement of complex stimulation channels to optimally distribute sensory information across the channels of a multi-channel tissue-stimulating prosthesis. A tissue-stimulating prosthesis may initially be associated with a set of complex stimulation channels. A stimulation efficiency is determined for each complex stimulation channel within the set of complex stimulation channels. A first complex stimulation channel from the set of complex stimulation channels that has an associated stimulation efficiency that is below a stimulation efficiency limit is identified. The first complex stimulation channel is combined with an adjacent/neighboring complex stimulation channel to create a combined complex stimulation channel. The combined complex stimulation channel replaces both the first complex stimulation channel and the adjacent complex stimulation channel within the set of complex stimulation channels.

20 Claims, 6 Drawing Sheets

| Contact | E1 | E2 | E3 | E4 | E5 | E6 | E7 | E8 | E9 | E10 | E11 | E12 | E13 | E14 | E15 | E16 | E17 | E18 | E19 | E20 | E21 | E22 | ECE |
|---|---|---|---|---|---|---|---|---|---|---|---|---|---|---|---|---|---|---|---|---|---|---|---|
| 472 { First Channel (E5) | -0.076 | 0.005 | -0.035 | -0.340 | 1.000 | -0.372 | -0.030 | -0.026 | -0.013 | -0.021 | 0.002 | 0.002 | -0.041 | 0.011 | -0.004 | 0.000 | -0.002 | 0.002 | 0.001 | -0.013 | 0.012 | -0.043 | -0.021 |
| 474 { Second Channel (E6) | -0.047 | -0.016 | -0.012 | -0.019 | -0.386 | 1.000 | -0.383 | -0.009 | -0.037 | 0.016 | -0.016 | -0.011 | 0.012 | -0.012 | -0.005 | -0.006 | 0.006 | -0.005 | -0.008 | 0.010 | -0.015 | -0.008 | -0.049 |
| 476 { Combined Channel (E5+E6) | -0.123 | -0.011 | -0.047 | -0.359 | 0.614 | 0.628 | -0.413 | -0.035 | -0.050 | -0.005 | -0.014 | -0.009 | -0.029 | -0.001 | -0.008 | -0.005 | 0.004 | -0.003 | -0.006 | -0.003 | -0.002 | -0.051 | -0.070 |

470

(58) Field of Classification Search
USPC .................................................... 607/57, 67
See application file for complete search history.

(56) References Cited

U.S. PATENT DOCUMENTS

| | | |
|---|---|---|
| 8,744,590 B2 | 6/2014 | Smith et al. |
| 2010/0198301 A1 | 8/2010 | Smith |
| 2011/0288613 A1 | 11/2011 | Smith et al. |
| 2015/0343217 A1* | 12/2015 | Smith ............... A61N 1/36032 607/57 |

OTHER PUBLICATIONS

Pfingst et al., "Detection of pulse trains in the electrically stimulated cochlea: Effects of cochlear health", Acoustical Society of America, J. Acoust. Soc. Am. 130 (6), Dec. 2011, 15 pages.

Nelson et al., "Forward-masked spatial tuning curves in cochlear implant users", Acoustical Society of America, J. Acoust. Soc. Am. 123 (3), Mar. 2008, 22 pages.

Long et al., "Examining the Electro-Neural Interface of Cochlear Implant Users Using Psychophysics, CT Scans, and Speech Understanding", Research Article, Journal of the Association for Research in Otolaryngology, JARO 15: 293-304 (2014), Apr. 2014, vol. 15, Issue 2, 12 pages.

de Balthasar et al., "Channel interactions with high-rate biphasic electrical stimulation in cochlear implant subjects", Hearing Research, vol. 182, Issues 1-2, Aug. 2003, 39th Workshop on Inner Ear Biology, 11 pages.

Cohen et al., "Spatial spread of neural excitation in cochlear implant recipients: comparison of improved ECAP method and psychophysical forward masking", Hearing Research, vol. 179, Issues 1-2, May 2003, 16 pages.

* cited by examiner

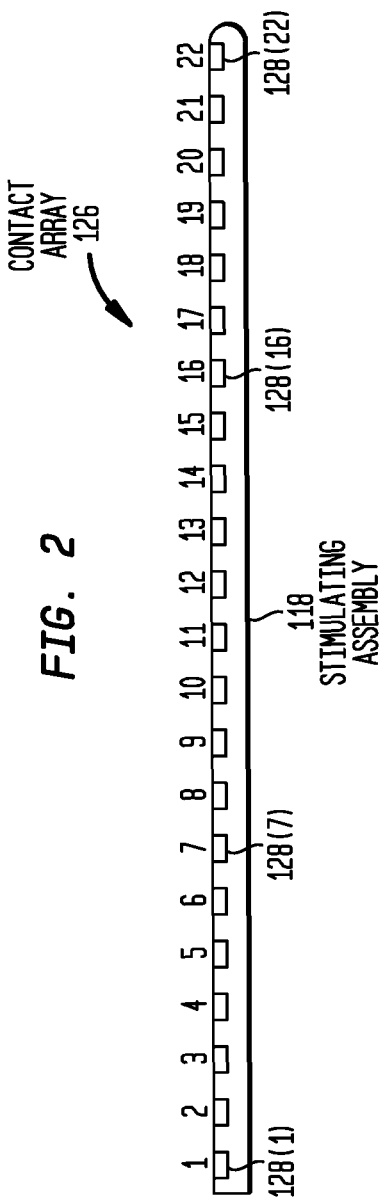

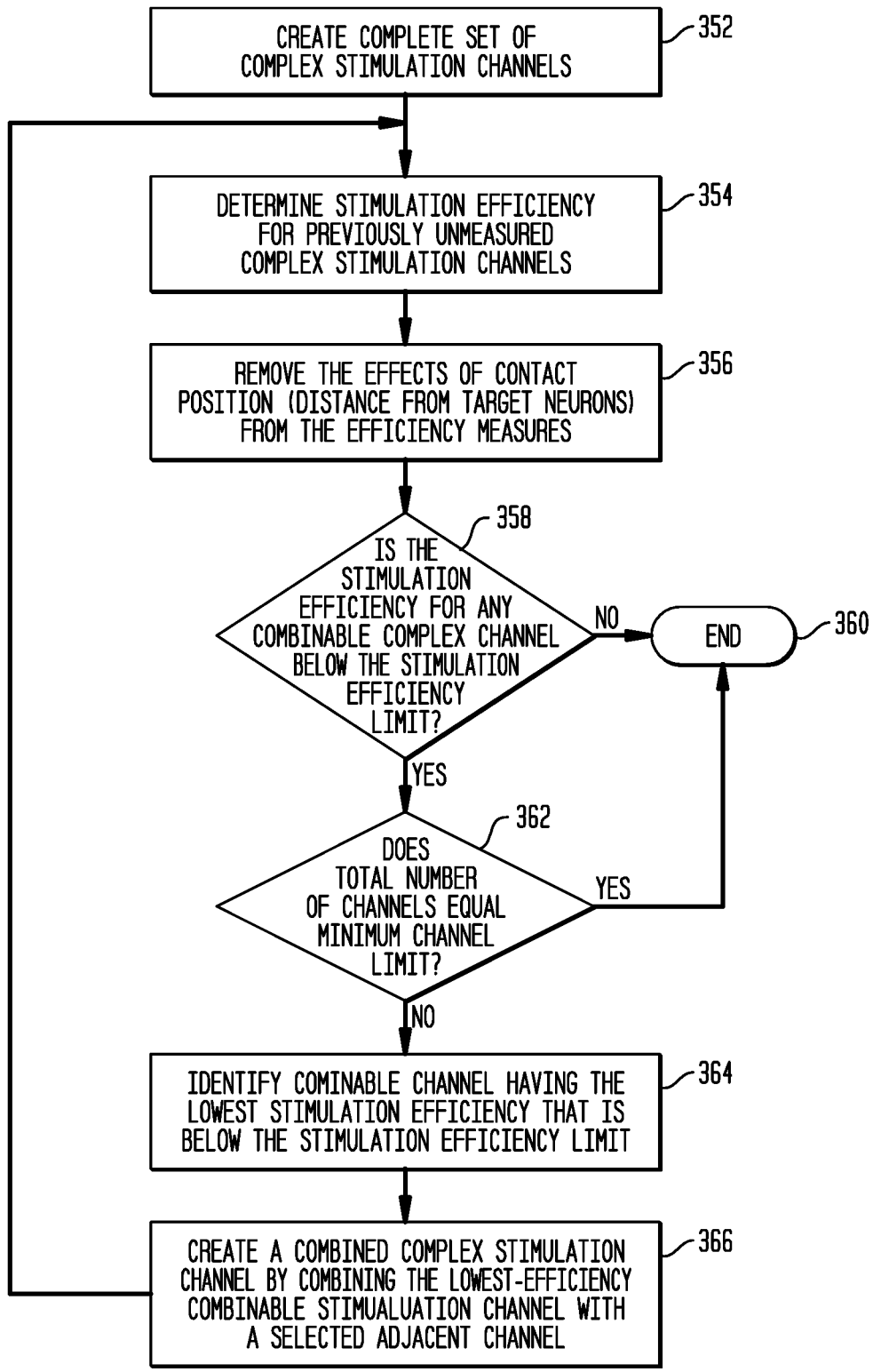

| Contact | E1 | E2 | E3 | E4 | E5 | E6 | E7 | E8 | E9 | E10 | E11 | E12 | E13 | E14 | E15 | E16 | E17 | E18 | E19 | E20 | E21 | E22 | ECE |
|---|---|---|---|---|---|---|---|---|---|---|---|---|---|---|---|---|---|---|---|---|---|---|---|
| 472 First Channel (E5) | -0.076 | 0.005 | -0.035 | -0.340 | 1.000 | -0.372 | -0.030 | -0.026 | -0.013 | -0.021 | 0.002 | 0.002 | -0.041 | 0.011 | -0.004 | 0.000 | -0.002 | 0.002 | 0.001 | -0.013 | 0.012 | -0.043 | -0.021 |
| 474 Second Channel (E6) | -0.047 | -0.016 | -0.012 | -0.019 | -0.386 | 1.000 | -0.383 | -0.009 | -0.037 | 0.016 | -0.016 | -0.011 | 0.012 | -0.012 | -0.005 | -0.006 | 0.006 | -0.005 | -0.008 | 0.010 | -0.015 | -0.008 | -0.049 |
| 476 Combined Channel (E5+E6) | -0.123 | -0.011 | -0.047 | -0.359 | 0.614 | 0.628 | -0.413 | -0.035 | -0.050 | -0.005 | -0.014 | -0.009 | -0.029 | -0.001 | -0.008 | -0.005 | 0.004 | -0.003 | -0.006 | -0.003 | -0.002 | -0.051 | -0.070 |

| Contact | E1 | E2 | E3 | E4 | E5 | E6 | E7 | E8 | E9 | E10 | E11 | E12 | E13 | E14 | E15 | E16 | E17 | E18 | E19 | E20 | E21 | E22 | ECE |
|---|---|---|---|---|---|---|---|---|---|---|---|---|---|---|---|---|---|---|---|---|---|---|---|
| 482 First Channel (E3+E4+E5) | -0.245 | -0.357 | 0.545 | 0.265 | 0.638 | -0.395 | -0.093 | -0.048 | -0.032 | -0.033 | -0.017 | -0.001 | -0.029 | -0.003 | -0.015 | 0.004 | -0.045 | -0.011 | -0.007 | -0.018 | 0.013 | -0.055 | -0.140 |
| 484 Second Channel (E2) | -0.418 | 1.000 | -0.388 | -0.006 | 0.004 | -0.012 | 0.018 | -0.060 | 0.004 | -0.005 | 0.004 | -0.029 | -0.041 | -0.011 | 0.005 | 0.004 | 0.004 | -0.002 | -0.004 | 0.001 | -0.004 | -0.005 | -0.049 |
| 486 Combined Channel (E2+E3+E4+E5) | -0.662 | 0.643 | 0.157 | 0.278 | 0.702 | -0.407 | -0.076 | -0.108 | -0.029 | -0.038 | -0.013 | -0.030 | -0.070 | -0.014 | -0.010 | 0.008 | -0.041 | -0.013 | -0.010 | -0.017 | 0.009 | -0.060 | -0.189 |

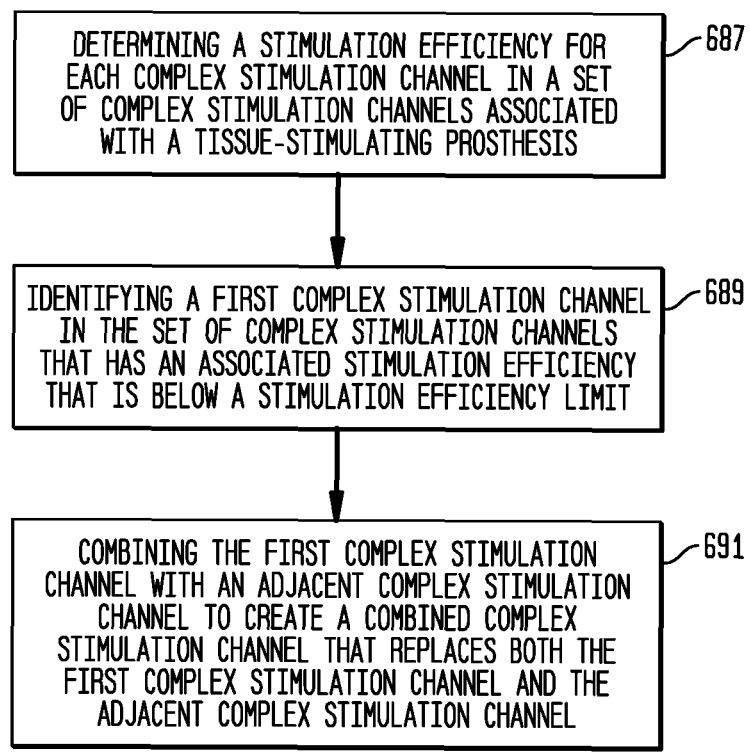

COMPLEX STIMULATION CHANNEL ARRANGEMENTS

CROSS-REFERENCE TO RELATED APPLICATIONS

This application claims priority to U.S. Provisional Application No. 62/096,193 entitled "Complex Stimulation Channel Arrangements," filed Dec. 23, 2014, the content of which is hereby incorporated by reference herein.

BACKGROUND

Field of the Invention

The present invention relates generally to tissue-stimulating prostheses.

Related Art

There are several types of medical devices that operate by delivering stimulation signals to the nerves, muscle or other tissue fibers of a recipient. These medical devices, referred to herein as tissue-stimulating prostheses, typically deliver stimulation to compensate for a deficiency in the recipient. For example, tissue-stimulating hearing prostheses, such as cochlear implants, are often proposed when a recipient experiences sensorineural hearing loss due to the absence or destruction of the cochlea hair cells, which transduce acoustic signals into nerve impulses. Auditory brainstem stimulators are another type of tissue-stimulating hearing prostheses that might be proposed when a recipient experiences sensorineural hearing loss due to damage to the auditory nerve.

SUMMARY

In one aspect presented herein, a method is provided. The method comprises: determining a stimulation efficiency for each complex stimulation channel in a set of complex stimulation channels associated with a tissue-stimulating prosthesis, identifying a first complex stimulation channel in the set of complex stimulation channels that has an associated stimulation efficiency that is below a stimulation efficiency limit, and combining the first complex stimulation channel with an adjacent complex stimulation channel to create a combined complex stimulation channel that replaces both the first complex stimulation channel and the adjacent complex stimulation channel.

In another aspect presented herein, a method is provided. The method comprises: determining the stimulation efficiency of a combined complex stimulation channel that is part of a set of complex stimulation channels associated with a tissue-stimulating prosthesis, identifying a first complex stimulation channel in the set of complex stimulation channels that has an associated stimulation efficiency that is below a stimulation efficiency limit, and combining the first complex stimulation channel with an adjacent complex stimulation channel to create an additional combined complex stimulation channel that replaces both the first complex stimulation channel and the adjacent complex stimulation channel.

In another aspect presented herein, a system is provided. The system comprises a memory, and a processor configured to: determine a stimulation efficiency for each complex stimulation channel in a set of complex stimulation channels associated with a tissue-stimulating prosthesis, identify a first complex stimulation channel in the set of complex stimulation channels that has an associated stimulation efficiency that is below a stimulation efficiency limit, and combine the first complex stimulation channel with an adjacent complex stimulation channel to create a combined complex stimulation channel that replaces both the first complex stimulation channel and the adjacent complex stimulation channel.

BRIEF DESCRIPTION OF THE DRAWINGS

Embodiments of the present invention are described herein in conjunction with the accompanying drawings, in which:

FIG. 2 is a schematic diagram of an intra-cochlear stimulating assembly configured for use in accordance with embodiments presented herein;

FIG. 3 is a detailed flowchart illustrating a method for optimizing complex stimulation channels in accordance with embodiments presented herein;

FIG. 4A is a table illustrating the consolidation of two complex stimulation channels in accordance with embodiments presented herein;

FIG. 4B is another table illustrating the consolidation of two complex stimulation channels in accordance with embodiments presented herein;

FIG. 6 is a high-level flowchart illustrating a method for optimizing complex stimulation channels in accordance with embodiments presented herein.

DETAILED DESCRIPTION

Presented herein are techniques for determining an arrangement (e.g., number, location, etc.) of complex stimulation channels to optimally distribute sensory information across the channels of a multi-channel tissue-stimulating prosthesis. More specifically, a tissue-stimulating prosthesis may initially be associated with a set of complex stimulation channels. A stimulation efficiency is determined for each complex stimulation channel within the set of complex stimulation channels. A first complex stimulation channel from the set of complex stimulation channels that has an associated stimulation efficiency that is below a stimulation efficiency limit is identified. The first complex stimulation channel is combined with an adjacent/neighboring complex stimulation channel to create a combined complex stimulation channel. The combined complex stimulation channel replaces (i.e., takes the place of) both the first complex stimulation channel and the adjacent complex stimulation channel within the set of complex stimulation channels.

As noted, there are several types of tissue-stimulating prostheses that deliver stimulation to compensate for a deficiency in a recipient. Merely for ease of illustration, the techniques presented herein are primarily described herein with reference to one type of tissue-stimulating prosthesis, namely a cochlear implant. It is to be appreciated that the techniques presented herein may be used with other tissue-stimulating prostheses including, for example, auditory brainstem stimulators, implantable pacemakers, defibrillators, functional electrical stimulation devices, pain relief stimulators, visual prostheses, other neural or neuromuscular stimulators, etc.

Figure 1:
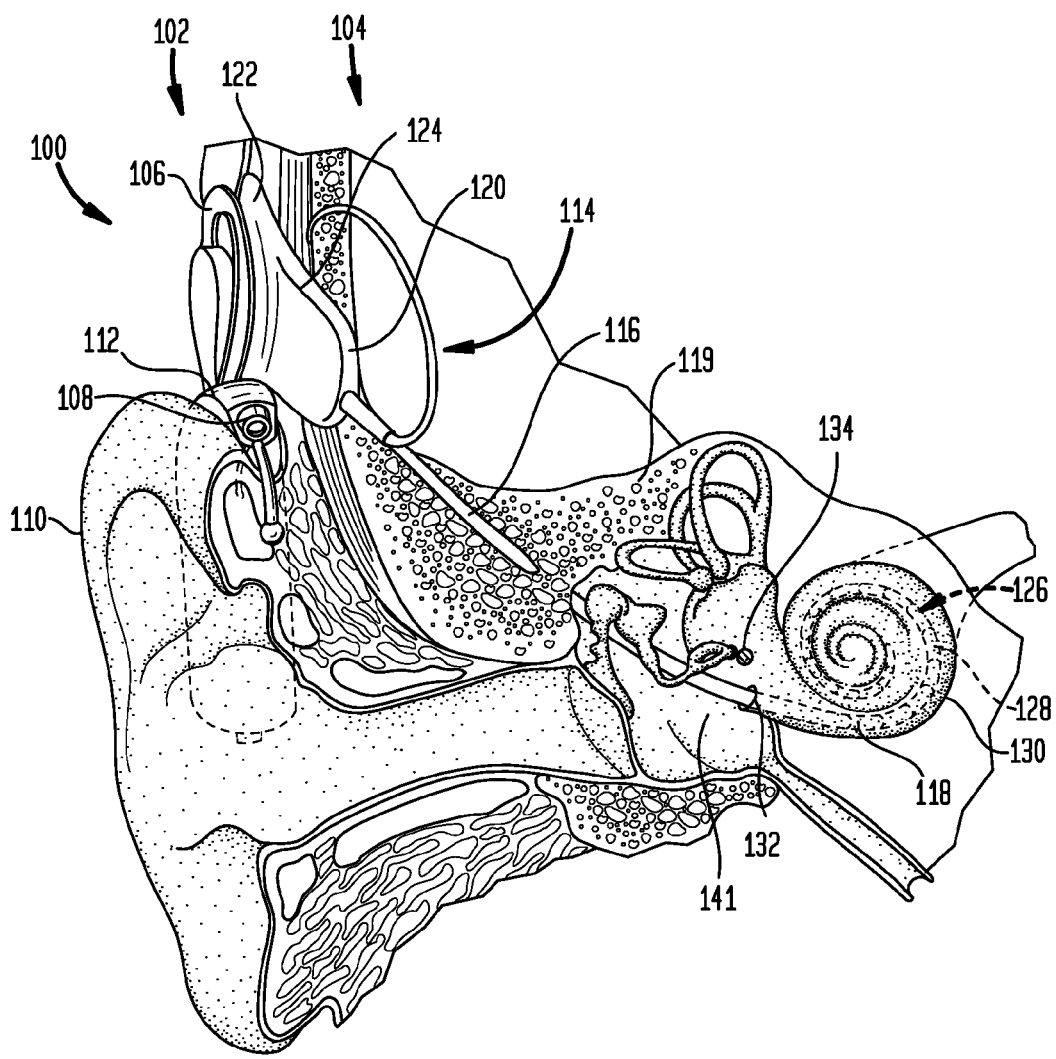
FIG. 1 is a schematic diagram of a cochlear implant configured for use in accordance with embodiments presented herein.

FIG. 1 is perspective view of an exemplary cochlear implant 100 that may be configured for use in optimizing an arrangement of complex stimulation channels in accordance with embodiments presented herein. The cochlear implant 100 includes an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more sound input elements 108 (e.g., microphones, telecoils, etc.) for detecting sound and a sound processing unit 112. The sound processing unit 112 may include, for example, a power source (not shown in FIG. 1) and a sound processor (also not shown in FIG. 1). The sound processor is configured to process electrical signals generated by a sound input element 108 that is positioned, in the depicted embodiment, by auricle 110 of the recipient. The sound processor provides the processed signals to external coil 106 via a cable (not shown in FIG. 1).

The implantable component 104 comprises an implant body 114, a lead region 116, and an elongate intra-cochlear stimulating assembly 118. The implant body 114 comprises a stimulator unit 120, an internal/implantable coil 122, and an internal receiver/transceiver unit 124, sometimes referred to herein as transceiver unit 124. The transceiver unit 124 is connected to the implantable coil 122 and, generally, a magnet (not shown) fixed relative to the internal coil 122.

The magnets in the external component 102 and implantable component 104 facilitate the operational alignment of the external coil 106 with the implantable coil 122. The operational alignment of the coils enables the implantable coil 122 to transmit/receive power and data to/from the external coil 106. More specifically, in certain examples, external coil 106 transmits electrical signals (e.g., power and stimulation data) to implantable coil 122 via a radio frequency (RF) link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is configured to be at least partially implanted in cochlea 130 and includes a plurality of longitudinally spaced intra-cochlear stimulating contacts 128. The contacts 128 collectively form a contact array 126 and may comprise electrical contacts and/or optical contacts. The stimulating assembly 118 may be a perimodiolar stimulating assembly or a non-perimodiolar stimulating assembly. A perimodiolar stimulating assembly is a stimulating assembly that is configured to adopt a curved configuration during and/or after implantation into the recipient's cochlea so as to have at least the distal section positioned close to the wall of the recipient's modiolus (i.e., close to the modiolar wall). One type of non-perimodiolar stimulating assembly is a lateral stimulating assembly that is configured to be implanted so as to be positioned along the lateral wall of the recipient's scala tympani (i.e., the wall that is opposite the modiolar wall). Another type of non-perimodiolar stimulating assembly is a mid-scala stimulating assembly which assumes a mid-scala position during or following implantation (i.e., positioned approximately midway between the modiolar wall and the lateral wall).

Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

In general, the sound processor in sound processing unit 112 is configured to execute sound processing and coding to convert a detected sound into a coded signal corresponding to electrical signals for delivery to the recipient. The coded signal generated by the sound processor is then sent to the stimulator unit 120 via the RF link between the external coil 106 and the internal coil 122. The stimulator unit 120 includes one or more circuits that use the coded signals, received via the transceiver unit 124, so as to output stimulation (stimulation current) via one or more stimulation channels that terminate in the intra-cochlear stimulating contacts 128. As such, the stimulation is delivered to the recipient via the intra-cochlear stimulating contacts 128. In this way, cochlear implant 100 stimulates the recipient's auditory nerve cells, bypassing absent or defective hair cells that normally transduce acoustic vibrations into neural activity.

Because the cochlea is tonotopically mapped, that is, partitioned into regions each responsive to stimulus signals in a particular frequency range, frequencies may be allocated to one or more electrodes of the stimulating assembly to generate an electric field in positions in the cochlea that are close to the region that would naturally be stimulated in normal hearing. This enables the cochlear implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit 112, that is, specific frequency bands with their associated signal processing paths, are mapped to a set of one or more stimulating contacts to stimulate a selected population of cochlea nerve cells (i.e., neurons of the cochlea). Such sets of one or more stimulating contacts for use in stimulation are referred to herein as "stimulation channels."

FIG. 2 illustrates a more detailed view of a portion of the stimulating assembly 118 of FIG. 1 comprising the array 126 of contacts 128, in accordance with one embodiment. FIG. 2 illustrates a specific arrangement in which stimulating assembly 118 comprises twenty-two (22) electrodes/contacts. As such, the contacts are labeled in FIG. 2 as contacts 128(1) through 128(22), where contact 128(1) is the most basal/proximal contact and contact 128(22) is the most distal/apical contact. The stimulating assembly 118 may also include or operate with an extra-cochlear electrode/contact (ECE) that is positioned outside of the recipient's cochlea. For ease of illustration, the extra-cochlear contact has been omitted from FIGS. 1 and 2.

Contact array 126 may be used to apply different modes of stimulation, such as, for example, monopolar, bipolar, tripolar, focused multi-polar ((FMP), a.k.a. "phased-array") stimulation, etc. The embodiments presented herein are described with reference to a cochlear implant in which the array 126 provides complex stimulation channels. As used herein, a "complex" stimulation channel, such as a tripolar or focused multi-polar stimulation channel, refers to a grouping of contacts that simultaneously deliver electrical charge/current to a recipient's nerve cells. The electrical charge is delivered across multiple contacts in order to focus stimulation at neurons located nearest to a "central contact" or "channel center" (i.e., the contact at the center of the focused multi-polar stimulation channel). A complex stimulation channel consists of three or more intracochlear electrode contacts and may include, for example, contacts 128(1)-128(5), 128(2)-128(8), all contacts 128(1)-128(22), etc. In general, the electrical charge is delivered simultaneously on the contacts across a given complex stimulation channel (e.g., twenty-two current sources are present in stimulator unit 120 to simultaneously deliver the charge at different contacts). However, the complex stimulation channels are generally activated in sequence (i.e., stimulation is delivered via a first complex stimulation channel, then stimulation is delivered via a second complex stimulation channel, and so on).

In complex stimulation channels, such as focused multi-polar stimulation channels, "weights" are assigned to all of the contacts that form part of the channel and the stimulation charge/current is applied using the weights. Therefore, the weights represent the direction and magnitude of current that is delivered at each contact of the complex stimulation channel. The weights may have positive values (meaning current is sourced/delivered at the associated contact) or negative values (meaning current is sunk at the associated contact) in the range of zero (0) to one (1).

Complex stimulation channels are effective for increasing channel independence and limiting electric field interactions between channels. However, in arrangements where the central contact of a complex stimulation channel is located in a region of relatively low neural density (i.e., regions in which the nerve cells are diseased, damaged, dead, etc.), the total charge required to elicit an equivalent neural response may be elevated and thus the stimulation channel has lower stimulation efficiency relative to other channels. In other words, if the central contact of a complex stimulation channel is positioned adjacent to an area of the cochlea that has relatively low neural density, the effectiveness of the complex stimulation channel will be lower than that of an equivalent complex stimulation channel having a central contact positioned adjacent to an area of the cochlea with relatively high neural density. In addition to requiring more stimulation charge, low-efficiency complex stimulation channels will also have lower channel capacity (i.e., information transfer rate) and lower channel independence relative to other complex stimulation channels with higher stimulation efficiency. Low neural density refers to an area of the cochlea with low survival of spiral ganglion cells due to, for example, disease, trauma, etc.

Therefore, a problem encountered in cochlear implants is how to determine an optimal arrangement (e.g., number, location, etc.) of focused multi-polar or other complex stimulation channels for recipients while taking into account, for example, varying levels of neural survival of spiral ganglion cells and/or distance of the electrode contacts to the modiolus. As such, presented herein are techniques that may be executed to optimally distribute sensory information across the focused multi-polar or other types of complex stimulation channels of a multi-channel tissue-stimulating prosthesis, such as a cochlear implant. As described further below, the techniques presented herein determine/measure and analyze channel efficiencies and "combine" low-efficiency channels with other channels to form fewer, but more efficient, channels. In general, combining complex stimulation channels in relatively low-efficiency regions acts to (1) broaden the area of stimulation/excitation, (2) increase stimulation efficiency, and (3) decrease the local number of channels. This serves to redistribute the stimulation channels in such a way that each channel more independently stimulates an even, and adequate, number of nerve cells (neurons) across the target sensory nucleus. By achieving a more uniform neural-channel density, information transfer to the brain is optimized for better sensory restoration.

FIG. 3 is a flowchart of a method 350 for optimizing complex stimulation channels in accordance with embodiments presented herein. For ease of illustration, method 350 is described with reference to cochlear implant 100 and stimulating assembly 118 of FIGS. 1 and 2 which, as noted, includes 22 contacts 128(1)-128(22). It is to be appreciated that the techniques presented herein may be used in other tissue-stimulating prostheses and with other arrangements of contacts.

Method 350 begins at 352 where a full/complete set of complex stimulation channels (e.g., focused multi-polar stimulation channels) are created for cochlear implant 100. The creation of a complete set of complex stimulation channels refers to the creation of a complex stimulation channel for each one of, or for a selected subset of, the electrodes/contacts 128(1)-128(22). Each complex stimulation channel may initially include one unique central contact. As noted above, within each complex stimulation channel, each contact has an assigned "weight" that represents the charge delivered via that contact of the complex stimulation channel. The weights of each channel in this original complete complex stimulation channel set may be normalized such that the central contact has a weight of +1.0.

A complete set of complex stimulation channels may be created in a number of different manners. In one example, recipient-specific current spread functions in the form of a matrix of transimpedance values between stimulated and idle contacts may be computed. The measured transimpedance values may then be used to compute an inverse matrix of transadmittance values. The matrix of transadmittance values may be used to determine the required vector of contact currents that will produce the desired vector of stimulating voltages of a channel (i.e., determine the channel weights for contacts of a complex stimulation channel). In another example, partial tripolar channels with a remote current fraction of 30% may be used (i.e. weight of +1.0 at the central electrode contact, −0.35 at the two flanking contacts, and −0.30 at the extracochlear, or far-field ground, electrode contact.) Other methods for creating complex stimulation channels are known in the art and are not described further herein.

Returning to the method of FIG. 3, at 354 the stimulation efficiency is determined (i.e., measured) for any previously unmeasured complex stimulation channels. Initially, the stimulation efficiency for all (or the initial subset) of the complex stimulation channels is unknown (i.e., all are unmeasured), thus the stimulation efficiency may be initially determined for all complex stimulation channels in the complete set of complex stimulation channels. In one embodiment, stimulation efficiency is defined by the "percept" divided by a channel's stimulus magnitude. The stimulus magnitude of a complex stimulation channel is the number used to scale the contact weights of the channel. This scaling is used to obtain the individual stimulus magnitudes to be applied to the individual contacts.

As noted, the stimulation efficiency is based on the stimulation magnitude (stimulus level) of the channel and not the individual contacts. Measurements can be made to find the stimulus magnitude for a channel that evokes a selected/target response, such as an equal percept across the different channels (e.g., detection threshold). Since the target response or percept is fixed across channels, the percept term can be dropped and the inverse of the stimulus magnitude can be used to determine the efficiency, as shown below in Equation 1.

$$\text{stimulation efficiency} = \frac{\text{percept}}{\text{stimulus magnitude}} \propto \frac{1}{\text{stimulus magnitude}} \quad \text{Equation 1}$$

In other words, measurements may be recorded to determine the stimulus level that is applied on a given complex stimulation channel to evoke a selected response. Examples of the types of measurements that can be used include, for example, perceptual detection thresholds, determination of stimulus magnitudes evoking equivalent sensory strength (e.g. equal perceptual loudness), etc. In a first example, the current level of a train of fixed duration biphasic current pulses is varied and the level that is just high enough to be reliably detected by the recipient is recorded. For this first example, "detection threshold" is the percept and "current level" is the stimulus magnitude and these measures are repeated for each channel. In a second example, the pulse width of each current pulse is varied for a train of biphasic current pulses and the pulse width that elicits a comfortably loud percept is recorded. For this second example, "comfortably loud" is the percept and "pulse width" is the stimulus magnitude. In general, once above the perceptual threshold, the percept of a given stimulus will increase with stimulus magnitude (e.g. get louder), whereas below the perceptual threshold, there is no percept regardless of stimulus magnitude (or until the stimulus magnitude reaches or exceeds threshold).

Additionally, rather than a fixed percept, a neural response level could be similarly used to determine the stimulation efficiency. Examples of the types of measurements that can be used in these neural response embodiments include, for example, detection of evoked neural potential thresholds (e.g., electrically evoked compound action potential (ECAP), electrically evoked auditory brainstem response (EABR), etc), or determination of fixed response amplitudes of electrically evoked potentials (e.g. ECAP, EABR, etc.). Similar to the perceptual measures, neural response magnitudes are absent for stimulus magnitudes below the threshold, but generally increase with increasing stimulus magnitudes above the threshold. In a first example, the stimulus magnitude is varied (e.g. current level) and the ECAP amplitude is measured. The stimulus magnitude is recorded that produces an ECAP amplitude of 10 μA and this is repeated for all channels. In a second example, a fixed level stimulus is delivered to each channel and the corresponding EABR amplitudes are recorded. In this second example, the stimulus is fixed rather than the response and thus the stimulation efficiency is proportional to the neural response amplitude.

It is to be appreciated that, in addition to measuring a stimulus level that evokes a certain response, stimulation efficiency may be approximated using other techniques that estimate the independence of a channel or the degree of neural density at a channel. For example, channel discrimination measures may be used to determine how well one channel is perceptually discriminated from an adjacent channel when matched for loudness. Typically, these judgments would be based on differences in perceived pitch, brightness, or timbre. Better discrimination between adjacent channels would correspond to higher stimulation efficiency. Additionally, channel interaction measures may be used to estimate stimulation efficiency, where adjacent channels with lower channel interactions would have higher stimulation efficiency. Furthermore, spatial tuning curves derived from perceptual forward masking or evoked potential measurements may be used to estimate how broadly a channel stimulates. Stimulation efficiency would be proportional to the slopes of the tuning curves (i.e. steeper slopes for more efficient channels) or inversely proportional to a channel's bandwidth (i.e. smaller bandwidth for more efficient channels). Alternative techniques may make use of estimates of local neural density to determine stimulation efficiency The psychophysical thresholds associated with certain complex stimulation channels, particularly, focused multipolar stimulation channels, increase significantly with the distance of a contact from the target neurons (e.g., at 11 dB/mm on average with standard deviation=7 dB/mm). Thus, in certain embodiments, at 356, the position of the contacts 128(1)-128(22) may be taken into account such that the effects of the contact position are removed from the stimulation efficiency measures. In one example, the effects of the contact position may be removed by using contact positions that are specific to the recipient (i.e., by first determining the position of the contacts relative to the target neurons and using this distance to adjust the stimulation efficiency measures to account for the specific contact placement). In another example, the effects of contact position may be removed by using average contact positions determined across a population of recipients (i.e., using predetermined average distances between the various contacts and the target neurons to adjust the stimulation efficiency measures).

At 358, the determined stimulation efficiencies are evaluated to determine if the stimulation efficiency of any complex stimulation channel with less than "N" center contacts is below a selected/established stimulation efficiency limit/threshold, where "N" is the maximum number of center contacts allowed in a "combined" channel. As described further below, when two or more complex stimulation channels are consolidated/combined, those two channels will be replaced with a newly created channel, referred to herein as a combined complex stimulation channel. A combined complex stimulation channel includes multiple center contacts that correspond to the center contacts of the component stimulation channels that were combined.

In certain examples, the number of center contacts, and thus the number of complex stimulation channels that may be combined, is limited to the value "N." Complex stimulation channels that have less than the maximum number of center contacts are sometimes referred to herein as "combinable" complex stimulation channels because, as described further below, these channels may be combined with other channels to reduce the total number of utilized complex stimulation channels (i.e., the number of channels forming a set of complex stimulation channels is reduced by one with each channel consolidation). Complex stimulation channels having "N" center contacts are not combinable with other channels since no additional center contacts may be added to the channel. In certain embodiments, "N" is equal to 3. Thus, in one specific example, at 358, channels that have less than 3 center contacts are the combinable complex stimulation channels that may be evaluated to determine if any of those channels have a stimulation efficiency below the stimulation efficiency limit. If there are no combinable complex stimulation channels that have a stimulation efficiency below the stimulation efficiency limit, then method 350 ends at 360.

In certain embodiments, the stimulation efficiency limit could be set based on empirical data. In one such example, the stimulation efficiency limit is constrained by a maximum stimulus magnitude of 20 nC per phase for perceptual detection threshold. For biphasic current pulses with fixed phase durations of 50 µs, this corresponds to a maximum current level of 0.4 mA. Thus for this example, any channel with a perceptual detection threshold greater than 0.4 mA (or 20 nC) would have a stimulation efficiency below the set limit. In other embodiments, the stimulation efficiency limit could be set based on the stimulation efficiency numbers obtained from the original focused multi-polar stimulation channels channel set (e.g. mean −1 standard deviation). For example, if the efficiency measures for a set of 10 multipolar channels were {131, 139, 137, 130, 126, 129, 114, 123, 101, 143}, then the mean −1 standard deviation of these numbers would be 114.9. Thus the channels with efficiency measures of 114 and 101 would fall below the mean −1 standard deviation stimulation efficiency limit.

If one or more combinable complex stimulation channels have a stimulation efficiency that is below the stimulation efficiency limit, then at 362 a determination is made as to whether the total number of channels equals a minimum channel limit (i.e., a threshold as to the minimum number of channels that may be present). If the total number of channels equals the minimum channel limit (e.g., eight (8) channels), then the method 350 ends at 360.

If the total number of channels does not equal that minimum channel limit, that is, if the number of channels is greater than the minimum number of channels, then method 350 moves to 364. Upon reaching 364, it has been determined that (1) there are one or more combinable complex stimulation channels that have a stimulation efficiency below the selected stimulation efficiency limit, and (2) the total number of channels present is above a minimum channel limit. Accordingly, at 364, from amongst the combinable complex stimulation channels (i.e., channels with less than "N" center contacts), the combinable complex stimulation channel having the lowest stimulation efficiency below the stimulation efficiency limit is identified. The combinable complex stimulation channel having the lowest stimulation efficiency below the stimulation efficiency limit is sometimes referred to herein as the lowest-efficiency combinable stimulation channel.

At 366, a merged/combined complex stimulation channel is created by combining the lowest-efficiency combinable stimulation channel with a selected adjacent/neighboring channel. The adjacent channels are the complex stimulation channels that are immediately adjacent to lowest-efficiency combinable stimulation channel (i.e., two adjacent channels, where one is a more basilar stimulation channel and one is a more apical distal channel). In certain examples, the adjacent channel with the highest stimulation efficiency of the adjacent channels is selected for combining with the lowest-efficiency combinable stimulation channel. However, it is to be appreciated that other techniques for selecting which adjacent channel to combine with the lowest-efficiency combination stimulation channel may be used in alternative embodiments. For example, the channel having the lowest (or highest) number of central contacts below "N" may be selected for combination with the lowest-efficiency combinable stimulation channel. Further details regarding the merging/combining of the lowest-efficiency combinable stimulation channel with an adjacent channel are provided below.

At 366, both the lowest-efficiency combinable stimulation channel and the adjacent channel are replaced in the focused multi-polar stimulation channel set by the combined complex stimulation channel. That is, two channels from the focused multi-polar stimulation channel set are consolidated and replaced by a single channel (i.e., a complex stimulation channel is removed from the set of complex stimulation channels). As such, after the consolidation of two complex stimulation channels into a combined complex stimulation channel, the number of channels with the complex stimulation channel set is reduced by one (1) stimulation channel. The set of the complex stimulation channel that includes the combined complex stimulation channel and the complex stimulation channels other than the combinable stimulation channel and the adjacent channel is sometimes referred to herein as an "adjusted" set of complex stimulation channels.

After consolidation of the lowest-efficiency combinable stimulation channel and the adjacent channel, method 350 returns to 354 where the stimulation efficiency for the combined complex stimulation channel is measured. Steps 356-366 may be repeated until a termination condition is met. As noted above, the termination conditions may include a determination that no combinable complex stimulation channels have a stimulation efficiency below a selected stimulation efficiency limit or a determination that the total number of channels has reached a minimum channel limit. Other termination conditions which are not shown in FIG. 3 may include, for example, a selected number of merger operations, a time limit, etc. As such, multiple adjusted sets of complex stimulation channels may be iteratively generated until a termination condition is reached. Upon identification of a termination condition, the most recent adjusted set of complex stimulation channels is the final set of complex stimulation channels that is used by the cochlear implant 100 to deliver stimulation to the recipient.

In accordance with embodiments presented herein, complex stimulation channels are combined by summing the weights associated with corresponding contacts of the component complex stimulation channels. For example, FIG. 4A is a table 470 illustrating the merger of a first complex stimulation channel 472 having contact 5 (E5) as its central contract with a second complex stimulation channel 474 having contact 6 (E6) as its central contact. Shown in table 470 are the weights associated with each of the contacts in the first and second complex stimulation channels.

Table 470 also illustrates a combined channel 476 formed from the consolidation of the component channels 472 and 474. As shown, the combined complex stimulation channel 476 has two central contacts that correspond to the central contacts of the component channels (i.e., central contacts E5 and E6) and the weights for the new channel are the sum of the weights from the first and second channels associated with each contact. In other words, the weights for contact 1 (E1) in the component channels 472 and 474 are added together, the weights for contact 2 (E2) in the component channels 472 and 474 are added together, and so on. As shown in FIG. 4A, the two central contacts will generally no longer have a weight of +1.0 after the component channels are combined.

FIG. 4B is a table 480 illustrating a second example in which a first complex stimulation channel 482 is combined with a second complex stimulation channel 484. In this example, the first complex stimulation channel 482 is a previously-combined complex stimulation channel having three central contacts (E3, E4, and E5) and the second complex stimulation channel 484 has contact 2 (E2) as its central contact. Shown in table 480 are the weights associated with each of the contacts in the first and second complex stimulation channels.

Table 470 also illustrates a combined channel 486 formed from the merger of the component channels 482 and 484. As shown, the combined channel 476 has four central contacts that correspond to the central contacts of the component channels (i.e., central contacts E2, E3, E4, and E5) and the weights for the new channel are the sum of the weights from the first and second channels associated with each contact. In other words, the weights for contact 1 (E1) in the component channels 482 and 484 are added together, the weights for contact 2 (E2) in the component channels 482 and 484 are added together, and so on. This is equivalent to summing the four original channels for central contacts E3, E4, E5, and E2.

In certain embodiments of the present invention, the frequency-to-channel assignments are updated to reflect a final set of complex stimulation channels. In other words, when complex stimulation channels are combined, the total number of complex stimulation channels decreases. Therefore, in certain embodiments, acoustic frequencies are reassigned so that they are distributed roughly equally across the final set of complex stimulation channels (e.g., equal on the Bark scale, the Greenwood function, or roughly equal according to the frequency importance functions from the articulation index or speech intelligibility index). However, in other embodiments, the original frequency-to-channel assignment remains fixed and combining channels would thus increase the bandwidth for the combined channels with multiple central electrodes.

Figure 5:
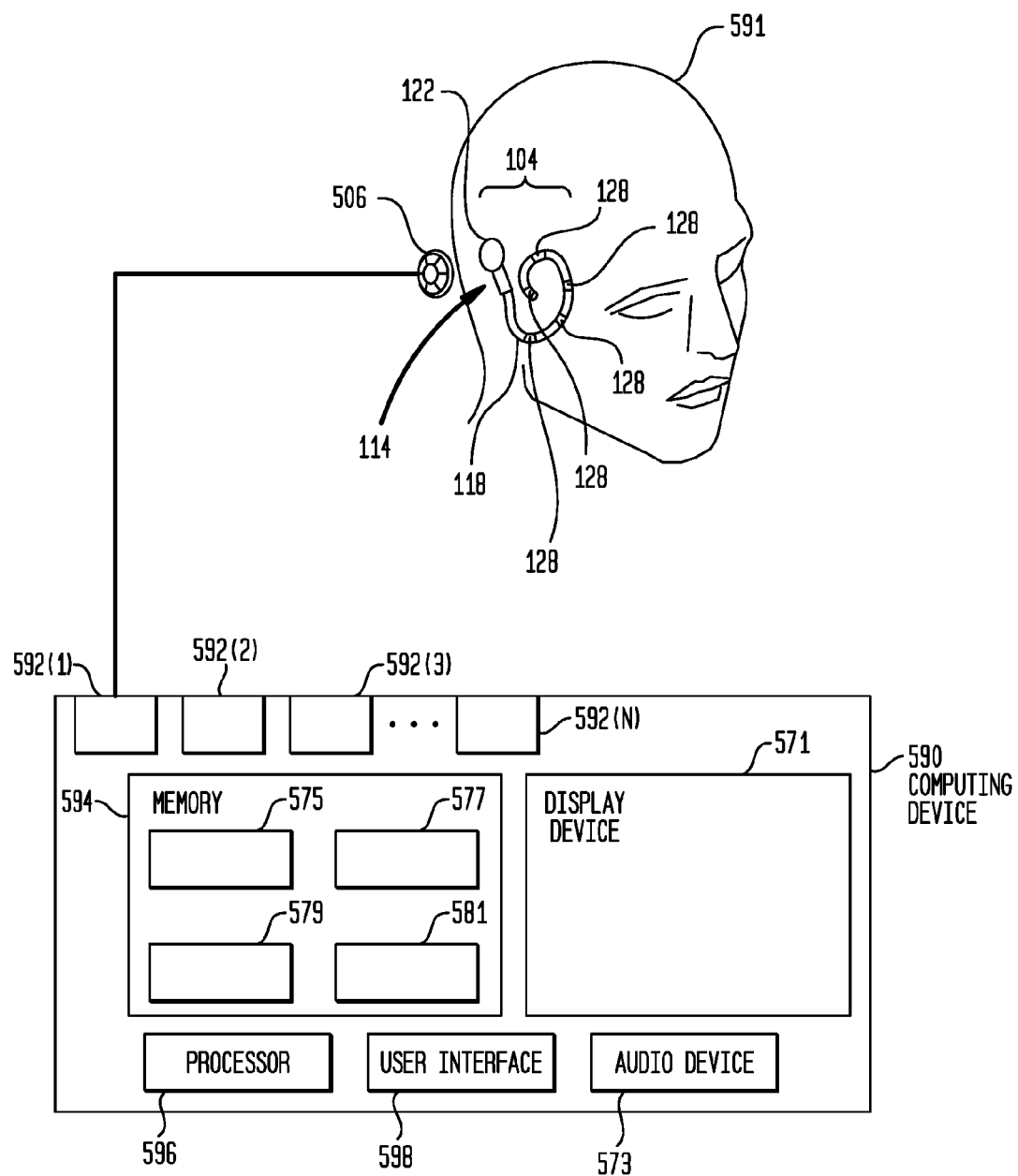
FIG. 5 is a block diagram of a computing device configured to implement techniques for optimizing the arrangement of complex stimulation channels in accordance with embodiments presented herein.

FIG. 5 is a block diagram of one exemplary arrangement for implementation of the complex stimulation channel optimization techniques in accordance with embodiments of the present invention. For ease of reference, the embodiment of FIG. 5 will be described with reference to implantable component 104 of FIG. 1 positioned in a recipient 591.

In the example of FIG. 5, the complex stimulation channel optimization functionality is implemented as part of computing device 590. The computing device 590 comprises a plurality of interfaces/ports 592(1)-592(N), a memory 594, a processor 596, a user interface 598, a display device (e.g., screen) 571, and an audio device (e.g., speaker) 573. The memory 594 comprises complex stimulation channel creation logic 575, stimulation efficiency measurement logic 577, evaluation logic 579, and complex stimulation channel combination logic 581. Although complex stimulation channel creation logic 575, stimulation efficiency measurement logic 577, evaluation logic 579, and complex stimulation channel combination logic 581 are shown as four separate blocks, it is to be appreciated that these logic blocks may be implemented as one integrated application/program.

The interfaces 592(1)-592(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 5, interface 592(1) is connected to an external coil 506 and/or an external device (not shown) in communication with the external coil. Interface 592(1) may be configured to communicate with the external coil 506 (or other device) via a wired or wireless connection (e.g., telemetry, Bluetooth, etc.). The external coil 506 may be part of an external component of a cochlear implant.

Memory 594 may comprise read only memory (ROM), random access memory (RAM), magnetic disk storage media devices, optical storage media devices, flash memory devices, electrical, optical, or other physical/tangible memory storage devices. The processor 596 is, for example, a microprocessor or microcontroller that executes instructions for the complex stimulation channel creation logic 575, stimulation efficiency measurement logic 577, evaluation logic 579, and complex stimulation channel combination logic 581. Thus, in general, the memory 594 may comprise one or more tangible (non-transitory) computer readable storage media (e.g., a memory device) encoded with software comprising computer executable instructions and when the software is executed (by processor 596) it is operable to perform the complex stimulation channel optimization operations described herein.

More specifically, in one embodiment, the complex stimulation channel creation logic 575 may be executed by the processor 596 to create a complete set of focused multi-polar stimulation channels. The complex stimulation channel creation logic 575, when executed, may generate signals/commands that cause stimulator unit 120 to, for example, generate stimulation current for delivery via the contacts 128 and to obtain electrical measurements at one or more contacts that may be used by the computing device 590 to create the complex stimulation channels. The stimulation efficiency measurement logic 577 may be executed by the processor 596 to determine the stimulation efficiency of one or more complex stimulation channels, such as the complete set of focused multi-polar stimulation channels and any combined complex stimulation channels. The complex stimulation channel creation logic 575, when executed, may generate signals/commands that cause stimulator unit 120 to, for example, generate stimulation current for delivery via the contacts 128 and to obtain electrical measurements at one or more contacts that may be used by the computing device 590 to determine the stimulation efficiency of channels.

The evaluation logic 579 may be executed by the processor 596 to evaluate the stimulation efficiencies to determine if a termination condition is present and/or to identify complex stimulation channels that could be combined with other complex stimulation channels. The complex stimulation channel combination logic 581 may be executed by the processor 596 to combine complex stimulation channels and to update a set of complex stimulation channels to replace the component channels with the combined channel (i.e., update a set of complex stimulation channels to reduce the set by one channel).

The computing device 590 may be any of a number of different hardware platforms configured to perform the techniques presented herein. In one embodiment, the computing device 590 is a computer (e.g., laptop computer, desktop computer, etc.) present within the operating theatre. In another embodiment, the computing device 590 is an intra-operative remote assistant. In a further embodiment, the computing device 590 is an off-the-shelf device, such as a mobile phone or tablet device, to which complex stimulation channel creation logic 575, stimulation efficiency measurement logic 577, evaluation logic 579, and complex stimulation channel combination logic 581 is downloaded as one or more applications or programs. In these various embodiments of FIG. 5, both control of the measurements and the display/notification of evaluation results occur through the computing device 590.

It is to be appreciated that this software implementation of FIG. 5 is merely illustrative, and that other implementations are possible. For example, in an alternative arrangement, complex stimulation channel creation logic 575, stimulation efficiency measurement logic 577, evaluation logic 579, and complex stimulation channel combination logic 581 may be implemented fully or partially as hardware elements, such as digital logic gates in one or more application-specific integrated circuits (ASICs).

FIG. 5 illustrates an example in which the channel optimization functionality is part of an external computing device. In alternative arrangements, the channel optimization functionality may be incorporated, for example, in an external or implantable component of a cochlear implant.

FIG. 6 is a flowchart of a method 685 in accordance with embodiments presented herein. Method 685 begins at 687 where a stimulation efficiency is determined for each complex stimulation channel in a set of complex stimulation channels associated with a tissue-stimulating prosthesis. At 689, a first complex stimulation channel from the set of complex stimulation channels that has an associated stimulation efficiency that is below a stimulation efficiency limit is identified. At 691, the first complex stimulation channel is combined with an adjacent complex stimulation channel to create a combined complex stimulation channel that replaces both the first complex stimulation channel and the adjacent complex stimulation channel.

Presented herein are techniques for using the consolidation of multiple complex stimulation channels to improve overall stimulation efficiency and reduce stimulation thresholds, while overcoming the presence of areas of low neural survival. These techniques are advantageous in identifying areas of low neural survival (i.e., areas that are not receptive to signals and where high thresholds may be required) in manner that optimizing the transfer of information to the recipient. In other words, the device/recipient interface is made more efficient since areas of low neural survival are compensated for by widening the center of the channels that are located in the vicinity of the low neural survival regions.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   determining a stimulation efficiency for each complex stimulation channel in a set of complex stimulation channels associated with a tissue-stimulating prosthesis, wherein each complex stimulation channel includes one or more electrodes;
   identifying a first complex stimulation channel in the set of complex stimulation channels that has an associated stimulation efficiency that is below a stimulation efficiency limit; and
   combining the first complex stimulation channel with an adjacent complex stimulation channel to create a combined complex stimulation channel that replaces both the first complex stimulation channel and the adjacent complex stimulation channel.

2. The method of claim 1, wherein the first complex stimulation channel and the adjacent complex stimulation channel each includes a single central contact, and wherein the combined complex stimulation channel includes two central contacts that correspond to the central contacts of the first complex stimulation channel and the adjacent complex stimulation channel.

3. The method of claim 1, wherein identifying the first complex stimulation channel from the set of complex stimulation channels that has an associated stimulation efficiency that is below a stimulation threshold limit comprises:
   identifying a plurality of complex stimulation channels in the set of complex stimulation channels that each have a stimulation efficiency below the stimulation efficiency limit; and
   selecting a complex stimulation channel having the lowest stimulation efficiency as the first complex stimulation channel.

4. The method of claim 1, further comprising:
   selecting the adjacent stimulation channel based on the stimulation efficiency of complex stimulation channels that are immediately adjacent to the first complex stimulation channel in the set of complex stimulation channels.

5. The method of claim 1, further comprising:
   removing effects of contact position when determining the stimulation efficiency for each of the complex stimulation channels in the set of complex stimulation channels.

6. The method of claim 1, wherein the combined complex stimulation channel forms part of an adjusted set of complex stimulation channels that includes the other channels in the set of complex stimulation channels other than the first complex stimulation channel and the adjacent complex stimulation channel.

7. The method of claim 6, wherein the tissue-stimulating prosthesis is an auditory prosthesis in which acoustic frequencies are allocated to each complex stimulation channel in the set of complex stimulation channels, and further comprising:
   re-distributing acoustic frequencies generally equally across the adjusted set of complex stimulation channels.

8. A method, comprising:
   determining the stimulation efficiency of a combined complex stimulation channel that is part of a set of complex stimulation channels associated with a tissue-stimulating prosthesis, wherein each complex stimulation channel includes one or more electrodes;
   identifying a first complex stimulation channel in the set of complex stimulation channels that has an associated stimulation efficiency that is below a stimulation efficiency limit; and
   combining the first complex stimulation channel with an adjacent complex stimulation channel to create an additional combined complex stimulation channel that replaces both the first complex stimulation channel and the adjacent complex stimulation channel.

9. The method of claim 8, wherein the first stimulation channel is the combined complex stimulation channel.

10. The method of claim 8, wherein identifying a first complex stimulation channel from the set of complex stimulation channels that has an associated stimulation efficiency that is below a stimulation threshold limit comprises:
    identifying a plurality of complex stimulation channels in the set of complex stimulation channels that each has a stimulation efficiency below the stimulation efficiency limit; and
    selecting a complex stimulation channel having the lowest stimulation efficiency as the first complex stimulation channel.

11. The method of claim 8, further comprising:
selecting the adjacent stimulation channel based on the stimulation efficiency of complex stimulation channels that are immediately adjacent to the first complex stimulation channel in the set of complex stimulation channels.

12. The method of claim 8, further comprising:
removing effects of contact position when determining the stimulation efficiency for each of the complex stimulation channels in the set of complex stimulation channels.

13. The method of claim 8, wherein the additional combined complex stimulation channel forms part of an adjusted set of complex stimulation channels that includes the other channels in the set of complex stimulation channels other than the first complex stimulation channel and the adjacent complex stimulation channel.

14. The method of claim 13, wherein the tissue-stimulating prosthesis is an auditory prosthesis in which acoustic frequencies are allocated to each complex stimulation channel in the set of complex stimulation channels, and further comprising:
re-distributing acoustic frequencies generally equally across the adjusted set of complex stimulation channels.

15. A system, comprising:
one or more network interface devices;
a memory; and
a processor configured to:
determine a stimulation efficiency for each complex stimulation channel in a set of complex stimulation channels associated with a tissue-stimulating prosthesis, wherein each complex stimulation channel includes one or more electrodes,
identify a first complex stimulation channel in the set of complex stimulation channels that has an associated stimulation efficiency that is below a stimulation efficiency limit, and
combine the first complex stimulation channel with an adjacent complex stimulation channel to create a combined complex stimulation channel that replaces both the first complex stimulation channel and the adjacent complex stimulation channel.

16. The system of claim 15, wherein to identify the first complex stimulation channel from the set of complex stimulation channels that has an associated stimulation efficiency that is below a stimulation threshold limit, the processor is configured to:
identify a plurality of complex stimulation channels in the set of complex stimulation channels that each has a stimulation efficiency below the stimulation efficiency limit; and
select a complex stimulation channel having the lowest stimulation efficiency as the first complex stimulation channel.

17. The system of claim 15, wherein the processor is further configured to:
select the adjacent stimulation channel based on the stimulation efficiency of complex stimulation channels that are immediately adjacent to the first complex stimulation channel in the set of complex stimulation channels.

18. The system of claim 15, wherein the processor is further configured to:
remove effects of contact position when determining the stimulation efficiency for each of the complex stimulation channels in the set of complex stimulation channels.

19. The system of claim 15, wherein the combined complex stimulation channel forms part of an adjusted set of complex stimulation channels that includes the other channels in the set of complex stimulation channels other than the first complex stimulation channel and the adjacent complex stimulation channel.

20. The system of claim 19, wherein the tissue-stimulating prosthesis is an auditory prosthesis in which acoustic frequencies are allocated to each complex stimulation channel in the set of complex stimulation channels, wherein the processor is further configured to:
re-distribute acoustic frequencies generally equally across the adjusted set of complex stimulation channels.

* * * * *